United States Patent
Huchet et al.

(10) Patent No.: US 8,987,169 B2
(45) Date of Patent: *Mar. 24, 2015

(54) STABILIZED HERBICIDAL COMPOSITION

(71) Applicant: Bayer CropScience LP, Research Triangle Park, NC (US)

(72) Inventors: Guillaume Huchet, Lawrence, KS (US); Tai-Teh Wu, Chapel Hill, NC (US); Daphne Miller, Liberty, MO (US); Karen L. Eagles, Raymore, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,512

(22) Filed: Mar. 24, 2014

(65) Prior Publication Data

US 2014/0323299 A1    Oct. 30, 2014

Related U.S. Application Data

(60) Continuation of application No. 13/776,301, filed on Feb. 25, 2013, now Pat. No. 8,716,185, which is a continuation of application No. 13/524,260, filed on Jun. 15, 2012, now Pat. No. 8,410,025, which is a division of application No. 11/810,201, filed on Jun. 5, 2007, now Pat. No. 8,232,231, which is a continuation-in-part of application No. 11/509,283, filed on Aug. 24, 2006, now Pat. No. 8,883,689, which is a continuation-in-part of application No. 11/295,757, filed on Dec. 6, 2005, now abandoned.

(51) Int. Cl.
*A01N 25/32* (2006.01)
*A01N 43/00* (2006.01)
*A01N 25/22* (2006.01)
*A01N 43/76* (2006.01)
*A01N 43/56* (2006.01)
*A01N 37/34* (2006.01)

(52) U.S. Cl.
CPC ............... *A01N 25/22* (2013.01); *A01N 43/76* (2013.01); *A01N 43/56* (2013.01); *A01N 37/34* (2013.01)
USPC ............ 504/105; 504/106; 504/107; 504/139

(58) Field of Classification Search
None
See application file for complete search history.

(56) References Cited

U.S. PATENT DOCUMENTS

| | | | |
|---|---|---|---|
| 5,264,411 A * | 11/1993 | Hewett et al. ................. | 504/130 |
| H0001942 H | 2/2001 | Theodoridis et al. | |
| 6,908,883 B2 | 6/2005 | Sievernich et al. | |
| 8,110,529 B2 * | 2/2012 | Frisch et al. .................. | 504/118 |
| 8,642,508 B2 * | 2/2014 | Wu et al. ....................... | 504/103 |
| 8,716,185 B2 * | 5/2014 | Huchet et al. ................. | 504/138 |
| 2002/0042345 A1 | 4/2002 | Kocur et al. | |
| 2004/0106519 A1 | 6/2004 | Ruegg | |
| 2007/0129251 A1 | 6/2007 | Wu et al. | |
| 2007/0259789 A1 | 11/2007 | Huchet et al. | |
| 2009/0131258 A1* | 5/2009 | Kumata et al. ............... | 504/136 |
| 2010/0048401 A1 | 2/2010 | Wu et al. | |
| 2012/0108424 A1 | 5/2012 | Wu et al. | |

FOREIGN PATENT DOCUMENTS

| | | | |
|---|---|---|---|
| GB | 2128090 | * | 4/1984 |
| RU | 2 260 947 | | 9/2005 |
| WO | 98/24321 | | 6/1998 |
| WO | 0078139 | | 12/2000 |
| WO | 2007/067472 | | 6/2007 |

OTHER PUBLICATIONS

Gaillard et al. FEBS Letters 352, 1994, 219-221.

* cited by examiner

*Primary Examiner* — Alton Pryor

(57) ABSTRACT

A stabilized herbicidal composition comprising fenoxaprop ester herbicide in combination with pyrasulfotole. The present disclosure also provides for a method of stabilizing herbicidal compositions.

21 Claims, 1 Drawing Sheet

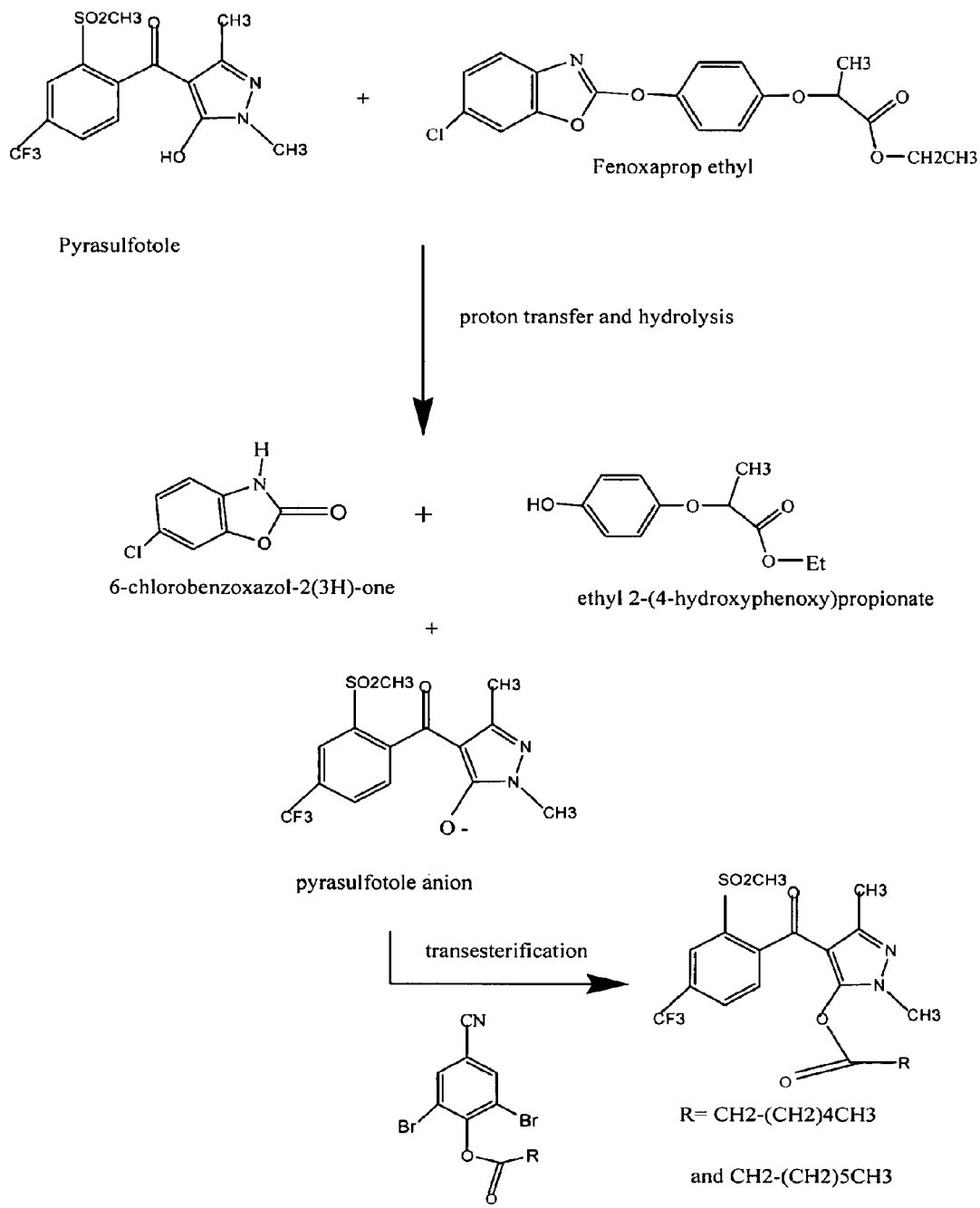

STABILIZED HERBICIDAL COMPOSITION

This Application is a Continuation Application of Ser. No. 13/776,301, filed Feb. 25, 2013, which is a Continuation Application of U.S. patent application Ser. No. 13/524,260, filed Jun. 15, 2012, which is a Divisional of U.S. patent application Ser. No. 11/810,201, filed Jun. 5, 2007, which is in turn a Continuation-in-part of U.S. patent application Ser. No. 11/509,283, filed Aug. 24, 2006, which is itself a Continuation-in-part of U.S. patent application Ser. No. 11/295,757, filed Dec. 6, 2005, the entire contents of each Application are herein incorporated by reference in their entirety for all purposes.

BACKGROUND OF THE INVENTION

1. Field of the Invention

The present invention relates generally to crop protection compositions and, in one embodiment, to crop protection compositions containing aryloxyphenoxypropionic esters and uses thereof.

2. Description of the Current Technology

A wide variety of herbicides are in use today. These known herbicides can be effective against different types of undesirable vegetation and can act in different ways. For example, some herbicides are particularly useful when applied to broad leaf plants while others are more useful when applied to grassy plants. Also, these different herbicides can perform their herbicidal function in different ways. For example, some herbicides may act as acetyl-CoA carboxylase inhibitors while others act in a completely different manner, such as acetolactate synthase inhibitors, or carotenoid biosynthesis inhibitors, or mitosis inhibitors, or photosynthesis inhibitors, just to name a few. In order to combat a wide variety of different types of undesirable vegetation, it is not uncommon to combine several different types of herbicides into a single herbicidal composition. This herbicidal composition can then be applied to a field in a single application without having to apply each of the herbicides individually.

An example of one particularly useful group of herbicides are aryloxyphenoxypropionic esters. Aryloxyphenoxypropionic esters typically act as acetyl-CoA carboxylase inhibitors. An example of such herbicides include fenoxaprop esters, such as fenoxaprop ethyl, commercially available from Bayer CropScience, LP. The fenoxaprop esters, such as fenoxaprop ethyl, are particularly useful for application to cereal crops to combat grassy weeds. A basic formula for fenoxaprop herbicides is shown in Formula I below.

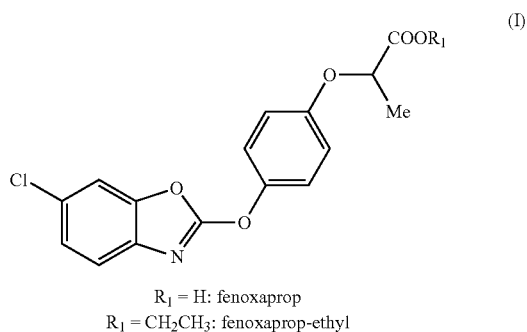

R₁ = H: fenoxaprop
R₁ = CH₂CH₃: fenoxaprop-ethyl

The fenoxaprop ester herbicides are quite well adapted for application to cereal crops and have found widespread acceptance. However, it has been observed that when a fenoxaprop ester herbicide, particularly fenoxaprop ethyl or a fenoxaprop lower alkyl ester, is mixed with certain other herbicides, the fenoxaprop ester herbicide can degrade more rapidly than if the fenoxaprop herbicide were not mixed with the other herbicides. This has been particularly observed when a fenoxaprop ester is mixed with herbicides that act as weak acids, such as pyrasulfotole and bromoxynil. This increased degradation of fenoxaprop esters can be disadvantageous to a farmer because it can decrease the useful shelf life of a fenoxaprop ester containing herbicidal composition. See FIG. 1 for example.

Therefore, it would be useful to provide a fenoxaprop ester containing herbicidal composition that reduces or eliminates the drawbacks associated with previous herbicidal compositions.

SUMMARY OF THE INVENTION

A herbicide composition comprises a fenoxaprop ester and a buffer system. The buffer system maintains the herbicidal composition at a pH in the range of 4 to 10, or 4 to 8, or 4.5 to 8, or 5 to 7.5, or 5.8 to 7.5. In one non-limiting embodiment, the fenoxaprop ester is fenoxaprop ethyl. The buffer system can comprise an amine-containing material, such as a tertiary amine. The herbicide composition can include other herbicides, such as weak acid herbicides, and can include one or more safeners.

BRIEF DESCRIPTION OF THE DRAWINGS

FIG. 1 is a schematic representation of the acid-catalyzed hydrolysis and transesterification reaction mechanism of the present invention.

DESCRIPTION OF THE PREFERRED EMBODIMENTS

As used herein, all numbers, such as but not limited to dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims may vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.5, 5.5 to 10, 2.3 to 7.3, etc. All references and publications referred to herein, such as but not limited to U.S. patents and published applications, are to be understood as being herein incorporated by reference in their entirety.

In one non-limiting embodiment, a herbicidal composition of the invention comprises an aryloxyphenoxypropionic ester, such as a fenoxaprop ester herbicide (optically active or racemic mixture), a buffer system, optionally one or more weak acid herbicides, and optionally one or more safeners.

Aryloxyphenoxypropionic esters have been described above. Non-limiting examples of aryloxyphenoxypropionic esters are described, for example, in U.S. Pat. Nos. 6,908,883 B2 and 6,887,827 B2. The present invention will be described with respect to the use of a fenoxaprop ester, such as fenoxaprop ethyl, in a herbicide composition. However, it is to be understood that the invention is not limited to use with fenoxaprop ethyl but is believed to be applicable to other aryloxyphenoxypropionic esters, e.g., fenoxaprop esters.

The buffer system can be a weak acid buffer system and can comprise a water-miscible acid and a water-miscible salt of the acid. In a highly advantageous embodiment of the invention, the water-miscible acid is a herbicide. By the term "weak acid" is meant an acid with a plc in the range of 0.1 to 10 at 25° C. The buffer system is configured to maintain the pH of the herbicidal composition in the range of 4 to 10, e.g., 4 to 8, e.g., 4.5 to 8, e.g., 5 to 7.5, e.g., 5.8 to 7.5. For example, the buffer system could maintain the pH of the herbicide composition in the range of 4 to 7, such as 5 to 7, such as 5 to 6.

The salt of the weak acid can be an amine or imine salt of the weak acid. Substantially non-nucleophilic conjugate amines are preferred to prepare the amine salts. Tertiary alkyl amines are most preferred, although secondary alkyl amines and primary amines may be used. The amine can also comprise primary, secondary, and/or tertiary amine function in any combination within the same molecule or the mixture of them. For example, the amine can be a tertiary amine or a trialkylamine in which the alkyl can be optionally substituted with a hydroxy group.

Generally one or more of the alkyl moieties of the amine has from 1 to 50 carbons, preferably from 1 to 10 carbons, and, in an alternative embodiment, has from 2 to 6 carbons. The alkyl group can be straight chained, branched, or cyclic alkyl. The one or more alkyl moieties can be, independent of one another, optionally substituted by one or more ether groups, e.g. alkoxy, hydroxyl groups, thiol groups, alkylthio, alkene, alkyne, amino, alkylamino, dialkylamino, or combinations of these functional groups that include a carbon to carbon double bond (i.e., an alkene) or carbon to carbon triple bond (i.e., an alkyne). The amine can be in the form of monoamine or diamine or polyamine. In a preferred embodiment, the one or more alkyl moieties of the amine may be hydroxylated, ethoxylated, diethoxylated, triethoxylated, or substituted with hydroxyethoxy or hydroxypropoxy groups wherein the number of ethoxy and propoxy groups may be from 1 to 60.

The composition can be in any formulation form, particularly a liquid composition, such as an emulsifiable concentrate, suspoemulsion, suspension concentrate, or a solution, such as an aqueous solution. In one non-limiting embodiment, an emulsifiable concentrate and a suspoemulsion is preferred.

The conjugate base of the amine salt may also serve as a surfactant in the composition, such as a nonionic surfactant or an ionic surfactant.

Representative conjugate amines and imines include one or more of the following: tertiary amines such as triethanolamine, triisopropanolamine; trialkylamines such as triethylamine, trimethylamine, tripropylamine, triisopropylamine, 1-octaneamine-N,N-dimethyl, N,N-dimethylcyclohexanamine, N,N-dimethyl-1-hexadecylamine, 1-dodeccanamine-N,N-dimethyl, ethyldiethanolamine, hexamethylenetetramine, N,N,N'',N''-tetrakis-(2-hydroxypropyl)ethylene diamine, dicocoalkyl-methylamine, didecylmethylamine, tridodecyamine, trihexadecylamine; monoalkyldimethylamines such as dodecyldimethylamine, hexadecyl-dimethylamine, octadecyl-dimethylamine, cocoalkyl-dimethylamine, soyalkyl-dimethylamine, soyaalkyl-dimethylamine, tallowalkyl-dimethylamine, hydrogenated tallowalkyl-dimethylamine, cottonseed alkyl-dimethylamine; ethoxylated alkylamines such as ethoxylated(n) cocoalkylamine, ethoxylated (n) tallowalkylamine, ethoxylated (n) soyaalkylamine, ethoxylated cottonseed amine, oleyl amine ethoxylate, ethoxylated(n) octadecylamine, (ethoxy group numbers n may be from 1 to 60), ethoxylated diamines, such as ethoxylated(n) N-tallow-1,3-diamineopropane, ethoxylated(n) N-tallow-1,3-diaminopropane, ethoxylated(n) N-tallow-1,3-diaminopropane, N,N-bis[α-ethyl-ω-hydroxypoly(oxyethylene)alkylamine; the poly (oxyethylene) content average 3 moles; the alkyl groups (C14-C18) are derived from tallow, or from soybean or cottonseed oil acids, or other crop or vegetable seeds oil acids. N,N-bis(2-hydroxyethyl)alkylamine, where the alkyl groups (C8-C18) are derived from coconut, cottonseed, soya, or tallow acids or other crops or vegetable seed acids; N,N-Bis 2-(ω-hydroxypolyoxyethylene)ethyl)alkylamine; the reaction product of 1 mole N,N-bis(2-hydroxyethyl)alkylamine and 3-60 moles of ethylene oxide, where the alkylgroup (C8-C18) is derived from coconut, cottonseed, soya, or tallow acids or other crop or vegetable seed acids. N,N-Bis-2-(ω-hydroxypolyoxyethylene/polyoxypropylene)ethyl alkylamine; the reaction product of 1 mole of N,N-bis(2-hydroxyethyl alkylamine) and 3-60 moles of ethylene oxide and propylene oxide, where the alkyl group (C8-C18) is derived from coconut, cottonseed, soya, or tallow acids or other crop seeds or vegetable seeds acids, N,N'-Bis,(2-hydroxyethyl)-C12-C18 alkylamine, N,N'-bis(polyoxyethylene)cetylamine, N,N'-Bis(polyoxyethylene)oleylamine, N,N'-bis(polyoxyethylene)stearylamine, N,N'-dinitropentamethylenetetramine, ethoxylated abietylamine. Secondary amine such as diethylamine, diisopropanolamine, dimethylamine, ditallowamine, dicocoalkylamine, dehydrogenated tallowalkylamine, didecylamine, dioctadecylamine, ethylethanolamine. Primary amine such as ethanolamine, butylamine, ethylamine, oleylamine, isopropylamine, isopropanolamine, propylamine, dodecanamine, primary N-alkylamine, where the alkyl group (C8-C18) is derived from coconut, cottonseed, soya or tallow acids, polyoxyethylated primary amine (C14-C18); the fatty amine is derived from an animal source and contains 3% water, the poly(oxyethylene) content average 20 moles, amines, C14-C15 alkyl, ethoxylated, amines, C16-C18 and C18 unsaturated, alkyl, ethoxylated. amines, tallowalkyl, ethoxylated with polyethylene, triethylene tetramine, ethylendiamine, diethyleneamine, diethylenetriamine, N-oleyl-1,3-propanediamine, tetramethylene pentamine, polypropylene glycol bis(2-aminopropyl)ether, 2-[(2-aminoethyl)amino]ethanol, 2-amino-2-methyl-1-propanol. Imines such as N,N'-disalicylidene-1,2-diaminopropane.

The herbicidal composition can include one or more weak acids. Non-limiting examples of representative weak acids include the following: phenols, phenol esters and mixtures of phenols and phenol esters, substituted phenols, conjugated diketones, conjugated triketones, carboxylic acids or their salts, such as alkylcarboxylic acids, phenylcarboxylic acids, phenoxy acetic acids, phenoxy propionic acids and their substituted and branched analogs and ester analogs.

Non-limiting examples of representative weak acids that are agriculturally acceptable herbicides include the following: pyrazole herbicides such as pyrasulfotole, nitrile herbicides such as bromoxynil, chloroxynil, or ioxynil, or a propesticidal precursor thereof, for example, bromoxynil octanoate or bromoxynil heptanoate, 2,4-D, Dicamba, MCPA, MCPP (mecoprop), or MCPB.

The herbicide composition may also include one or more agriculturally acceptable safener(s), such as but not limited to mefenpyr, isoxadifen, fenchlorazole, or cloquintocet, just to name a few.

Fenoxaprop ethyl when mixed with a weak acid herbicide (like pyrasulfotole) tends to degrade, e.g., hydrolyze, over time. In order to combat this degradation, a buffer system in accordance with the invention is introduced to the composition. An amine-containing buffer system, such as triethanolamine, triethylamine, and/or triisopropanolamine, has been found to be particularly useful.

In one non-limiting embodiment, the composition comprises (by weight percent based on the total weight of the composition) 3 wt. % to 6 wt. % pyrasulfotole, 7 wt. % to 10 wt. % fenoxaprop-ethyl, 1 wt. % to 4 wt. % triethanolamine, and, optionally, 3 wt. % to 6 wt. % mefenpyr. The remainder of the composition can comprise fillers as are conventional in the art. The components can be emulsified and/or can be dissolved or dispersed in any conventional solvent.

Four Part Stable Herbicidal Combination: Fenoxaprop ethyl with Particular Salts of 2,4-D/MCPP-P/Dicamba.

A four part combination of fenoxaprop ethyl with certain phenoxy herbicides, in particular the combination of fenoxaprop-p ethyl with 2,4-D, MCPP-P and Dicamba exhibited chemical instability in either water based formulations or solvent based formulations. However, such instability has been found to have been overcome when the fenoxaprop-p ethyl is combined with specific forms of the additional herbicides.

In particular, when fenoxaprop-p ethyl is combined with certain salts of the phenoxy herbicides, the resulting combination is stable. Such a combination is the combination of fenoxaprop-p ethyl with the triisopropanolamine ("TIPA") salt of 2,4-D, and the potassium salt of MCPP-P and the potassium salt of Dicamba. The inventors postulate that this combination eliminates or minimizes free proton in the mixture which free proton operates to degrade the fenoxaprop-p ethyl via an undesirable acidic hydrolysis of the fenoxaprop-p ethyl, as shown in FIG. 1 hereto and as described in PCT US/2006/046200 filed Dec. 4, 2006 which is hereby incorporated herein in its entirety by reference.

In the four part herbicidal combination of this embodiment of the present invention, the components may be present in the following ranges of percent by weight:

0.2 to about 2.0 wt % fenoxaprop-p ethyl
2.0 to about 20.0 wt % TIPA salt of 2,4-D
0.7 to about 8 wt % potassium salt of MCPP-P
0.2 to about 4.0 wt % potassium salt of dicamba.

In one embodiment of the present invention, for example, the levels as salts may be about the following percents by weight:

About 4.91 wt % for 2,4-D,
About 1.55 wt % for MCPP,
About 0.77% wt % for Dicamba, and
About 0.41 wt % for fenoxaprop.
Acid to salt conversion factors for may be:
About 1.86 wt % for 2,4-D,
About 1.17 wt % for MCPP, and
About 1.17 wt % for Dicamba.

In terms of a salt to acid conversion, conversions of about the following may be employed:

2,4-D Salt to Acid Conversion: 4.91 wt %/1.86 wt %=2.64 wt % acid,
MCPP Salt to Acid Conversion: 1.55 wt %/1.17 wt %=1.32 wt % acid,
Dicamba salt to Acid Conversion: 0.77 wt %/1.17 wt %=0.66 wt % acid.

Triethylamine may optionally be added in about a 3:1 ratio to fenoxaprop to improve stability.

In the following examples, the four part combination of fenoxaprop-p ethyl, TIPA salt of 2,4-D, potassium salt of MCPP-P and potassium salt of Dicamba were tested for stability and are compared with the combination of fenoxaprop-p ethyl with the non-salt forms of 2,4-D, MCPP-P and Dicamba.

EXAMPLE 1

Four Part Mixture of Fenoxaprop-p Ethyl/TIPA Salt of 2,4-D/Potassium Salt of Dicamba/Potassium Salt of MCPP-P Exhibiting Improved Stability A micro-emulsion of Fenoxaprop-p Ethyl, 2,4-D TIPA salt, Dicamba potassium salt and MCPP-P potassium was prepared.

TABLE 1

| INGREDIENTS |
|---|
| Fenoxyprop-p Ethyl, 0.41 wt % |
| TIPA salt of 2,4-D, 4.91 wt % |
| Potassium salt of Dicamba, 0.77 wt % |
| Potassium salt of MCPP-P, 1.55 wt % |
| [1] Alkyl alcohol ethoxylate, 1.0 wt % |
| [2] Anionic/nonionic detergent blend, 4.5 wt. % |
| [3] Microbiocide based on isothiazolinones, 0.15 wt % |
| [4] Acetate ester, C 6-8 alcohol, branched, 3.5 wt % |
| [5] Silicone antifoam emulsion, 0.01 wt % |
| Glycerine, 3.9 wt % |
| Water, Balance |

[1] Genopol X 060 alkylalcohol ethoxylate commercially available from Clariant Corporation.
[2] Agent 3088-92 anionic/nonionic detergent blend commercially available from Stepan Company.
[3] Acticide 820 commercially available from Acti-Chem Specialties Inc.
[4] Exxate 700 acetate ester, C 6-8 alcohol, branched commercially available from Chemcentral Corporation
[5] Anti foam 8830 FG Silicone antifoam emulsion commercially available from Harcros Chemicals Inc.

In the formulation of Table 1, the TWA salt of 2,4-D is used directly, but the potassium salts of Dicamba and MCPP-P are formed in situ starting with their acid forms which are converted to salt form by the addition of potassium hydroxide.

The mixture was tested for long-term storage stability by subjecting separate samples to different temperatures for two weeks and eight weeks. The following test results were obtained and are shown in Table 2.

TABLE 2

| | avg. Wt % | avg. Wt % | avg. Wt % | avg. Wt % |
|---|---|---|---|---|
| | | Active ingredient name | | |
| | 2,4-D acid | Dicamba acid | MCPP-P acid | fenoxaprop-p ethyl |
| 2 weeks @ 0° C. | 2.81 | 0.73 | 1.42 | 0.46 |
| 2 weeks @ room temp. | 2.82 | 0.73 | 1.41 | 0.46 |
| change from 0° C. | 0.36% | 0% | −0.70% | 0% |
| 2 weeks @ 54° C. | 2.86 | 0.79 | 1.43 | 0.42 |
| change from 0° C. | 1.78% | 8.22% | 0.70% | −8.70% |
| 8 weeks @ 0° C. | 2.81 | 0.66 | 1.39 | 0.47 |
| 8 weeks @ room temp. | 2.86 | 0.69 | 1.41 | 0.46 |
| change from 0° C. | 1.78% | 4.55% | 1.44% | −2.13% |
| 8 weeks @ 40° C. | 2.90 | 0.70 | 1.44 | 0.43 |
| change from 0° C. | 3.20% | 6.06% | 3.60% | −8.51% |

Although the potassium salts of MCPP-P and Dicamba were formed in situ as described above, it is customary to measure the acid equivalent in determining the stability of the herbicidal composition, as was done here.

EXAMPLE 2

Comparative Example of Fenoxaprop-P Ethyl/2,4-d Acid/Dicamba Acid/MCCP-P Acid

A mixture of fenoxaprop-p ethyl, 2,4-D dimethyamine (DMA) salt, Dicamba DMA salt and MCPP-P DMA salt was prepared in a similar manner as in Table 1 but without using the specific salts for 2,4-D, MCPP-P and Dicamba of the invention (see Table 3 below).

TABLE 3

INGREDIENTS

Fenoxyprop-p Ethyl, 0.41 wt %
2,4-D DMA salt, 3.34 wt %
Dicamba DMA salt, 0.60 wt %
MCPP-P DMA salt, 1.78 wt %
[1] Alkyl alcohol ethoxylate, 1.0 wt %
[2] Anionic/nonionic detergent blend, 4.5 wt. %
[3] Microbiocide based on isothiazolinones, 0.15 wt %
[4] Acetate ester, C 6-8 alcohol, branched, 4.5 wt %
[5] Silicone antifoam emulsion, 0.01 wt %
Glycerine, 3.9 wt %
Water, Balance

[1] Genopol X 060 alkylalcohol ethoxylate commercially available from Clariant Corporation.
[2] Agent 3088-92 anionic/nonionic detergent blend commercially available from Stepan Company.
[3] Acticide 820 commercially available from Acti-Chem Specialties Inc.
[4] Exxate 700 acetate ester, C 6-8 alcohol, branched commercially available from Chemcentral Corporation
[5] Antifoam 8830 FG Silicone antifoam emulsion commercially available from Harcros Chemicals Inc.

The DMA salt forms of 2,4-D, Dicamba and MCPP-P were selected over their acid forms because the DMA salt forms are believed to be able to provide the proton that results in the degradation of fenoxaprop ethyl illustrated in FIG. 1, and yet still be formulated in a water based formulation to provide for a more direct comparison with the formulation of Table 1.

The mixture was tested for long-term storage stability by subjecting separate samples to different temperatures for one week. The following test results were obtained and shown in Table 4.

TABLE 4

| | avg. Wt % | avg. Wt % | avg. Wt % | avg. Wt % |
| --- | --- | --- | --- | --- |
| | Active ingredient name | | | |
| | 2,4-D acid | Dicamba acid | MCPP-P acid | fenoxaprop-p ethyl |
| Initial analysis | 2.77 | 0.55 | 1.57 | 0.41 |
| 1 week @ 0° C. | 2.70 | 0.53 | 1.63 | 0.36 |
| change from initial | −2.53% | −3.64% | 3.82% | −12.2% |
| 1 week @ 54° C. | 2.80 | 0.56 | 3.25 | 0.038 |
| change from initial | 1.08% | 1.82% | 107.0% | −90.73% |
| 1 week @ room temp. | 2.77 | 0.53 | 2.04 | 0.28 |
| change from initial | 0.0% | −3.64% | 29.94% | −31.71% |

Again, as stated above, in accordance with custom, the acid equivalent was measured to determine the stability of the herbicidal composition, as was done here.

As can be seen from Table 4, there was a significant drop in the concentration of fenoxaprop-ethyl in Example 2 over Example 1. The foregoing examples clearly show the superior stability of the combination of fenoxaprop-p ethyl with the TIPA salt of 2,4-D, potassium salt of MCPP-P and potassium salt of Dicamba.

The present invention is not limited to these salt forms, and any other salt forms that provide the desired stabilization are within the scope of the present invention. For example, the salt form of 2,4-D may include a triethylamine salt form, a triisopropanolamine salt form, a triethanolamine salt form and combinations thereof. Similarly, the salt forms of MCCP and Dicamba can include other salt forms, such as the potassium salt forms, a sodium salt form, a lithium salt form and combinations thereof.

Stabilized Combination of Fenoxaprop-p Ethyl with Bromoxynil Mixed Esters.

In an alternative embodiment of the present invention, the inventors have found that a combination of fenoxaprop-p ethyl with bromoxynil mixed esters may be similarly stabilized with the addition of triethanolamine. The inventors postulate that the triethanolamine operates to stabilize the bromoxynil octanoate ("BO") and the bromoxynil heptanoate ("BH") found in the bromoxynil mixed esters. Improved stability of the fenoxaprop-ethyl was also observed. While not limited to such an application, such a combination is believed to be particularly effective at control of crabgrass and broad leaf weed control on turf, particularly in the form of an emulsifiable concentrate.

In the following example, the combination of fenoxaprop-p ethyl with bromoxynil mixed esters was compared in both a stabilized form (with triethanolamine) and non-stabilized form (with no triethanolamine). The percent change in fenoxaprop-p ethyl ("FPE"), BO and BH were observed in a 50 degree C. accelerated stability study at 4 weeks.

EXAMPLE 3

Comparison of Stabilized and Non-Stabilized Combination of Fenoxaprop-p Ethyl with Bromoxynil Mixed Esters

TABLE 5

INGREDIENTS

Fenoxyprop-p Ethyl, 4.340 wt %
Bromoxynil mixed esters, 13.44 wt %
Triethanolamine, 0 wt %
[1] alkyl alcohol ethoxylate, 6 wt %
[2] castor oil ethoxylated, 2 wt %
[3] Oxirane, 2-methyl-, polymer with oxirane, momo [tris(1-phenylethyl)phenyl]ether, 2 wt %
2-ethyl hexanol, 15 wt %
[4] Aromatic solvent, Balance

[1] Genopol X 080 alkylalcohol ethoxylate commercially available from Clariant Corporation.
[2] Emulsogen EL 400 commercially available from Clariant Corporation.
[3] Soprophor 796 P, commercially available from Rhodia Corporation
[4] A200 commercially available from Exxon Corporation A herbicidal composition comprising fenoxaprop-p ethyl, bromoxynil mixed esters but with no triethanolamine was formed as shown in Table 5 above.

Similarly, a herbicidal composition comprising fenoxaprop-p ethyl, bromoxynil mixed esters but with triethanolamine as a stabilized was formed as shown in Table 6, below.

TABLE 6

| INGREDIENTS |
| --- |
| Fenoxyprop-p Ethyl, 4.340 wt % |
| Bromoxynil mixed esters, 13.44 wt % |
| Triethanolamine, 0.10 wt % |
| [1] alkyl alcohol ethoxylate, 6 wt % |
| [2] castor oil ethoxylated, 2 wt % |
| [3] Oxirane, 2-methyl-, polymer with oxirane, momo [tris(1-phenylethyl)phenyl]ether, 2 wt % |
| 2-ethyl hexanol, 15 wt % |
| [4] Aromatic solvent, Balance |

[1] Genopol X 080 alkylalcohol ethoxylate commercially available from Clariant Corporation.
[2] Emulsogen EL 400 commercially available from Clariant Corporation.
[3] Soprophor 796 P, commercially available from Rhodia Corporation
[4] A200 commercially available from Exxon Corporation The percent change in fenoxaprop-p ethyl ("FPE"), BO and BH were observed for both compositions in a 50 degree C. accelerated stability study at 4 weeks, and are compared in Table 7 below.

TABLE 7

Fenoxaprop p-ethyl + Bromoxynil MEO EC Stability at 4 weeks; % change vs 0 degree C.

| % BH | % change BH | % BO | % change BO | % FPE | % change FPE | Temp | pH | TEA % |
| --- | --- | --- | --- | --- | --- | --- | --- | --- |
| 5.68 |  | 5.81 |  | 4.42 |  | 0 | 4.42 | 0 |
| 5.66 | −0.352112676 | 5.78 | −0.516351119 | 4.4 | −0.452488688 | RT |  |  |
| 5.45 | −4.049295775 | 5.59 | −3.786574871 | 4.27 | −3.393665158 | 40 |  |  |
| 5.1 | −10.21126761 | 5.25 | −9.638554217 | 4.08 | −7.692307692 | 50 |  |  |
| 5.56 |  | 5.65 |  | 4.41 |  | 0 | 7.2 | 0.05 |
| 5.59 | 0.539568345 | 5.69 | 0.707964602 | 4.42 | 0.22675737 | RT |  |  |
| 5.59 | 0.539568345 | 5.61 | −0.707964602 | 4.4 | −0.22675737 | 40 |  |  |
| 5.54 | −0.35971223 | 5.6 | −0.884955752 | 4.36 | −1.133786848 | 50 |  |  |

In the above table, "RT" stands for room temperature.

As may be observed, the percent change in the FPE, BH and BO in the composition stabilized with triethanolamine was far less than that of the unstabilized composition, indicating far greater stability with the stabilized composition.

The present invention is not limited only to the combination of fenoxaprop esters such as fenoxaprop-p ethyl with bromoxynil MEO. The present inventors have found that when any other herbicide (or for that matter, when any other hydrogen donating or protonating agent) is mixed with a fenoxaprop ester, such other herbicide or protonating agent can cause the degradation of the fenoxaprop ester in accordance with a degradation mechanism that is the same as or similar to that shown in FIG. 1. Indeed, given that the esterification process to develop ester type herbicides from acids often contain residual acid, it is often the case that such ester type herbicides contain some acid form of the ester itself, which can act as a catalyst to cause the degradation of the fenoxaprop ester. Whether caused from the acid form of the ester type herbicides and/or from the presence of other protonating agents such as other protonating or weak acid herbicides, they act as latent weak acids which will eventually cause the degradation of the fenoxaprop ester. Therefore, it is believed that the stabilizing agents disclosed above in this specification, see for example Paragraph 0011 et seq., will operate to stabilize and prevent or limit this degradation, which could also be termed an acid catalyzed hydrolysis of the fenoxaprop ester.

Examples of some of the herbicidal compounds that can be mixed with the fenoxaprop esters which can function as weak acids or such latent weak acids include pre and post emergent broad leaf herbicides and combinations thereof. Pre-emergent broad leaf herbicides include but are not limited to isoxaben, thiencarbazone-methyl, tembotrione, atrazine, pendimethalin, prodiamine, dithiopyr, N-bicyclic alkylaminotriazines and isomers including optical isomers, enantiometric isomers and the racemates and combinations thereof. Post emergent broad leaf herbicides include but are not limited to 2,4-D, dicamba, MCPP (& MCPP-p), MCPA, fluroxypyr, triclopyr, penoxsulam, florasulam, thiencarbazone-methyl, metribuzin, sulfentrazone, carfentrazone, atrazine, bentazon, bromoxynil, 2,4-DP, clopyralid, iodosulfuron, metsulfuron, mesosulfuron-methyl and combinations thereof.

As may be appreciated by those skilled in the art, the novel herbicidal compositions of the present invention may be mixed with other ingredients such as but not limited to, fertilizers, fungicides, insecticides including miticides and nematicides, plant growth regulators, insect grown regulators and combinations thereof.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A stabilized herbicidal composition, comprising:
  (a) fenoxaprop ester herbicide;
  (b) pyrasulfotole;
  (c) bromoxynil mixed ester,
  (d) at least one safener selected from the group consisting of mefenpyr, isoxadifen, fenchlorazole, and cloquintocet, and
  (e) stabilizer selected from the group consisting of triethanolamine, triethylamine, triisopropanolamine, and combinations thereof; wherein the amine stabilizes the fernoxaprop ester herbicide and the bronoxynil mixed ester.

2. The herbicidal composition of claim 1, wherein the fenoxaprop ester herbicide comprises fenoxaprop-p ethyl.

3. The herbicidal composition of claim 1, wherein the bromoxynil mixed ester comprises bromoxynil octanoate.

4. The herbicidal composition of claim 1, wherein the bromoxynil mixed ester comprises bromoxynil heptanoate.

5. The herbicidal composition of claim 1, wherein the bromoxynil mixed ester comprises a combination of bromoxynil octanoate and bromoxynil heptanoate.

6. The herbicidal composition of claim 5, wherein the fenoxaprop ester herbicide comprises fenoxaprop-p ethyl and wherein the herbicidal compounds are present in the ranges of about:

0.5 to about 10 wt % fenoxaprop-p ethyl, 5 to about 40 wt % bromoxynil mixed esters, and 0.01 to about 5 wt % triethanolamine.

7. The herbicidal composition of claim 1, wherein the stabilizer comprises triethanolamine.

8. The herbicidal composition of claim 1, wherein the stabilizer comprises triethylamine.

9. The herbicidal composition of claim 1, wherein the stabilizer comprises triisopropanolamine.

10. The herbicidal composition of claim 1, wherein the herbicidal composition is formulated as one selected from the group consisting of a liquid composition, emulsifiable concentrate, suspoemulsion, suspension concentrate, and an aqueous solution.

11. The herbicidal composition of claim 1, comprising mefenpyr as said at least one safener.

12. The herbicidal composition of claim 1, further comprising at least one surfactant.

13. A method of controlling weeds in crops, comprising: applying the herbicidal composition of claim 1 to crops.

14. The method of claim 13, wherein the crops are cereal crops.

15. A method of controlling grassy weeds in crops, comprising: applying the herbicidal composition of claim 1 to crops and/or grassy weeds growing in crops.

16. A method of improving the stability of an herbicidal composition, comprising:
combining
   a) a fenoxaprop ester herbicide;
   b) one or more weak acid herbicides selected from the group consisting of bromoxynil, bromoxynil ester, bromoxynil mixed ester, and mixtures thereof;
   c) at least one stabilizer selected from the group consisting of triethanolamine, triethylamine, triisopropanolamine, and combinations thereof,
   (d) pyrasulfotole, and
   (e) at least one safener selected from the group consisting of mefenpyr, isoxadifen, fenchlorazole, and cloquintocet; wherein the amine stabilizes the fernoxaprop ester herbicide and the bronoxynil, bronoxynil ester, bromoxynil mixed ester, or mixtures thereof.

17. A method of claim 16, wherein the one more weak acids herbicides comprises bromoxynil mixed ester.

18. The method of claim 16, wherein the fenoxaprop ester herbicide is fenoxaprop-p ethyl.

19. The method of claim 17, wherein the bromoxynil mixed ester comprises a combination of bromoxynil octanoate and bromoxynil heptanoate.

20. The method of claim 16, wherein the at least one stabilizer comprises triethanolamine.

21. The method of claim 16, wherein after combining, the at least one stabilizer is present in the herbicidal composition in an amount of about 0.01 to about 5%.

* * * * *